(12) United States Patent
Nivoliez

(10) Patent No.: US 11,197,899 B2
(45) Date of Patent: *Dec. 14, 2021

(54) COMPOSITIONS FOR TREATING CANDIDIASIS INFECTIONS

(71) Applicant: NEXBIOME THERAPEUTICS, Clermont-Ferrand (FR)

(72) Inventor: Adrien Nivoliez, Yolet (FR)

(73) Assignee: NEXBIOME THERAPEUTICS, Clermont-Ferrand (FR)

( * ) Notice: Subject to any disclaimer, the term of this patent is extended or adjusted under 35 U.S.C. 154(b) by 122 days.

This patent is subject to a terminal disclaimer.

(21) Appl. No.: 16/077,114

(22) PCT Filed: Mar. 1, 2017

(86) PCT No.: PCT/EP2017/054701
§ 371 (c)(1),
(2) Date: Aug. 10, 2018

(87) PCT Pub. No.: WO2017/148975
PCT Pub. Date: Sep. 8, 2017

(65) Prior Publication Data
US 2019/0046593 A1    Feb. 14, 2019

(30) Foreign Application Priority Data

Mar. 1, 2016 (FR) ...................... 1651717

(51) Int. Cl.
| | | |
|---|---|---|
| *A61K 35/747* | (2015.01) | |
| *A61K 38/06* | (2006.01) | |
| *A61K 31/198* | (2006.01) | |
| *A61P 15/02* | (2006.01) | |
| *A61K 9/00* | (2006.01) | |
| *A61K 9/20* | (2006.01) | |
| *A61K 33/04* | (2006.01) | |

(52) U.S. Cl.
CPC .......... *A61K 35/747* (2013.01); *A61K 9/0034* (2013.01); *A61K 9/2054* (2013.01); *A61K 9/2086* (2013.01); *A61K 31/198* (2013.01); *A61K 33/04* (2013.01); *A61K 38/063* (2013.01); *A61P 15/02* (2018.01); *A61K 9/0002* (2013.01); *A61K 2300/00* (2013.01)

(58) Field of Classification Search
CPC ................................................. A61K 35/747
See application file for complete search history.

(56) References Cited

U.S. PATENT DOCUMENTS

| | | | |
|---|---|---|---|
| 6,093,394 A | 7/2000 | Chrisope | |
| 6,468,526 B2 | 10/2002 | Chrisope | |
| 7,807,440 B2 | 10/2010 | Molin et al. | |
| 2002/0044926 A1 | 4/2002 | Reid et al. | |
| 2010/0151026 A1 | 6/2010 | Liu et al. | |

FOREIGN PATENT DOCUMENTS

| | | | | |
|---|---|---|---|---|
| FR | 2992973 A1 | 1/2014 | | |
| WO | WO84/04675 A1 | 12/1984 | | |
| WO | WO9846261 A1 | 10/1998 | | |
| WO | WO2000/035465 A2 | 6/2000 | | |
| WO | WO2006/045475 A1 | 5/2006 | | |
| WO | WO2014/009330 A1 | 1/2014 | | |
| WO | WO2014009330 A1 | 1/2014 | | |
| WO | WO-2014009349 | * | 1/2014 | ............ A61K 33/04 |
| WO | WO2014009349 A1 | 1/2014 | | |
| WO | WO-2016003870 A1 | * | 1/2016 | ........... A61K 9/2095 |

OTHER PUBLICATIONS

International Search Report of PCT/EP2017/054701; dated May 15, 2017; Bochelen, Damien.

Sobel "A Prospective Study of the Efficacy of Maintenance Ketoconazole Therapy"; Recurrent Vulvovaginal Candidiasis; The New England Journal of Medicine; Dec. 4, 1986; vol. 315, No. 23; pp. 1455-1458.

Fischer "Chronic vulvovaginal candidiasis: What we know and what we have yet to learn" Australasian Journal Dermatolog; 2012; vol. 53; pp. 247-254.

Petrova et al. "*Lactobacillus* species as biomarkers and agents that can promote various aspects of vaginal health"; Frontiers in Physiology; Mar. 25, 2015; vol. 6, No. 81; pp. 1-18.

Kern et al. "Preventive treatment of vulvovaginal candidosis with vaginal probiotic (Gynophilus®—Lcr Regenerans®): results of the observational study Candiflore"; La lettre du Gynécologue; No. 370; Mar. 2012; pp. 34-37.

Yue et al. "The dynamic changes of vaginal microecosystem in patients with recurrent vulvovaginal candidiasis: a retrospective study of 800 patients"; Arch Gynecol Obstet; 2015.

Murina et al. "Can Lactobacillus fermentum LF10 and Lactobacillus acidophilus LA02 in a slow-release vaginal product be useful for prevention of recurrent vulvovaginal candidiasis?" A clinical study; J Clin Gastroenterol; vol. 48, sup. 1; Nov./Dec. 2014; pp. S102-S105.

Coudeyras et al. "Taxonomic and Strain-Specific Identification of the Probiotic Strain *Lactobacillus rhamnosus* 35 within the *Lactobacillus casei* Group"; Appl. Environ. Microbiol.; 2008; vol. 74, No. 9; pp. 2679-2689.

\* cited by examiner

*Primary Examiner* — Bin Shen

(74) *Attorney, Agent, or Firm* — BCF LLP

(57) ABSTRACT

The present invention relates to a composition comprising as antifungal active agent at least $2 \cdot 10^{10}$ CFU of lactobacilli and a sulfur-containing compound for use as a first-line treatment for candidiasis and for recurrent candidiasis.

14 Claims, 5 Drawing Sheets

COMPOSITIONS FOR TREATING CANDIDIASIS INFECTIONS

CROSS-REFERENCE TO RELATED APPLICATIONS

This United States National Stage Patent Application of International Application No. PCT/EP2017/054701 filed on Mar. 1, 2017 which claims priority from French Patent Application No. 1651717 filed Mar. 1, 2016, the content of which is herein incorporated in its entirety by reference.

FIELD OF THE INVENTION

The present invention relates to the combined use of high concentrations of lactobacilli with specific concentrations of a sulfur-containing compound for the treatment, particularly the first-line treatment, of candidiasis and of recurrent candidiasis. The combination according to the invention can replace treatment by a chemical antifungal.

The invention is, for example, suitable for the treatment, particularly the first-line treatment, of vaginal candidiasis and recurrent vaginal candidiasis.

STATE OF THE ART

In a healthy woman, the urogenital flora comprises nearly 50 different species of microorganisms. Among these microorganisms, 95% of the population is composed of various strains of lactobacilli, also called "Döderlein's bacilli". These lactobacilli help protect against pathogens by various mechanisms, including the production of hydrogen peroxide, lactic acid and bacteriocins, the inhibition of adhesion and the spreading of pathogens. In particular, these lactobacilli maintain an acidic pH by producing lactic acid from the glycogen present in the vaginal mucus. Thus, the growth of numerous pathogens of the vaginal microbiota, such as *Gardnerella vaginalis, Prevotella bivia, Neisseria gonorrhoeae, Mycoplasma*, and *Mobiluncus*, is inhibited.

The normal vaginal microbiota is thus principally composed of lactobacilli forming a protective biofilm on the surface of the mucous membrane. The lactobacilli most frequently observed in the vagina are notably *Lactobacillus crispatus, Lactobacillus jensenii, Lactobacillus vaginalis, Lactobacillus iners* and *Lactobacillus gasseri*.

Vulvovaginal candidiasis (VVC) is a mycotic infection linked to excessive fungal growth in a normal microbiota. 85-95% of VVC are linked to *Candida albicans*. Vulvovaginal candidiasis affects 70-75% of women at least once during their reproductive years (1); about 40-50% will have a second episode. The incidence of recurrent vulvovaginal candidiasis (defined as at least 4 episodes per year, including two confirmed by mycological examination) has been estimated at 5-8%. This benign ailment has a very negative impact on patients' quality of life and generates significant healthcare expenditures. Such pathology is difficult to treat because of the multifactorial pathogenesis of this affection.

The appearance of VVC and its propensity to recur are real public health problems and represent significant health costs. Current treatments against VVC, based on the use of antifungals, are often associated with side effects, such as the development of bacterial vaginosis, and induce many recurrences (2).

New therapeutic developments should be directed toward a broader consideration of the pathology by taking into account its specific environment and the causes of its appearance. Thus, in the past few years, the characteristics of the vaginal microbiota have been specifically studied. This microbiota is dominated by the genus *Lactobacillus*, present in about 70% of women, each individual species of which constitutes 99% of the ribotypes observed in a woman (3). Probiotic products have been developed and tested for preventing recurrences of VVC (4, 5, 6) via the re-establishment of the balance of the vaginal microbiota. These products do not act directly against the pathogen responsible for the pathology but on the prevention of a new dysbiosis which may be induced by the antifungal treatment itself or by other external elements.

The oral or vaginal administration of 'beneficial' lactobacilli has been described to promote vaginal health. In particular, the patent applications WO 84/04675, WO 2000/035465, US 2002/0044926 and WO 2006/045475 describe the oral or vaginal administration of lactic bacteria to promote vaginal health and to prevent recurrences of vulvovaginal candidiasis.

The preferred lactobacilli are *Lactobacillus rhamnosus, Lactobacillus crispatus* and *Lactobacillus vaginalis*. The U.S. Pat. Nos. 6,093,394, 6,468,526 and 7,807,440, as well as the patent application US 2010/0151026, describe the administration of specific *Lactobacillus crispatus* strains.

These lactobacilli may be administered in lyophilized form or in solution, and optionally in combination with other active agents.

The patent applications WO2014/009349 and WO 2014/009330 describe the use of thiosulfate to potentiate the anti-pathogenic effect of lactobacilli. In these applications, thiosulfate is added in the culture medium of the *lactobacillus*, before lyophilization, at an optimal concentration of 113 g/L for about $10^8$ CFU/mL of lactobacilli (Formulation A). This addition makes it possible to potentiate the anti-pathogenic effect of lactobacilli, following a preliminary culture step. In all the tests, the inocula are prepared according to the following protocol:

Preparation of inocula:
  Probiotic product: 0.2 g of the lyophilizate is placed in 20 mL of MRS broth in an incubator at 37° C. for 48 hours;
  Pathogenic strain: 0.2 mL is placed in 20 mL of Sabouraud broth at 25° C. for 48 hours;
Contacting of inocula: 5 mL of the pathogenic strain is placed with 5 mL of the probiotic strain;
Measurements: the pathogen and the probiotic are counted at $T_0$, $T_{4\,h}$, $T_{24\,h}$ and $T_{28\,h}$. The count of the lactobacilli strains remains constant and that of the pathogen decreases.

These applications show that the addition of thiosulfate in the culture medium before lyophilization of the *lactobacillus* strain, at a concentration ranging from 1 g/L to 113 g/L, makes it possible to potentiate the anti-pathogenic effect of these lactobacilli, which were prepared beforehand by pre-culture for 48 hours before being contacted with the pathogen. Without this pre-culture step, no inhibition can be observed in the time following co-culture.

These applications show that the addition of thiosulfate makes it possible to envisage the use of potentiated lactobacilli to recolonize the vaginal microbiota and to prevent the regrowth of pathogenic agents and thus recurrences. They do not make it possible to envisage the use of potentiated lactobacilli, formulated in a pharmaceutical composition, in the first-line treatment of VVC, in view of the need to pre-culture the strain before use, which represents a non-adaptability of the composition to act immediately on the pathogen (and thus to exert a curative action as an antifungal would exert) and on the contrary an adaptability of the composition to exert a barrier effect to recolonization by the pathogen after an antifungal treatment.

In these applications, the lactobacilli concentrations indicated generally range from $10^7$ to $10^{10}$ CFU/g of composition, the concentration of $10^8$ CFU/mL before lyophilization being the preferred concentration employed in the examples (Formulation A).

Despite this use in the prevention of recurrences of VVC, the first-line use of lactobacilli strains as substitutes for antifungals is not allowed, notably considering that the proportion of lactobacilli does not vary during the development of the pathogen and of the pathology.

Surprisingly, it was noted that a pharmaceutical composition comprising a specific concentration of lactobacilli and of sulfur-containing compound could be used in the first-line treatment of candidiasis and of recurrent candidiasis. The invention describes in particular vulvovaginal candidiasis and recurrent vulvovaginal candidiasis.

Moreover, the current chemical treatments (antibiotics and antifungals) do not maintain the balance of the microbiota and may promote the emergence of side effects such as the development of bacterial vaginosis and numerous recurrences (2). This invention will make it possible by its composition to prevent the risks of recurrences. The invention developed thus makes it possible by the use of a probiotic strain to inhibit specifically the pathogens responsible for these pathologies, while maintaining the lactobacillary microbiota characteristic of an asymptomatic woman (2). The use of a natural biological product, unlike chemical products, does not generate dysbiosis ascribable to the current treatments and thus promotes the prevention of recurrences.

SUMMARY OF THE INVENTION

The invention relates to the use of a specific concentration of lactobacilli (concentration $\geq 2 \cdot 10^{10}$ CFU per dose), outside the usual uses of these products, combined with a sulfur-containing compound. This invention allows us to propose a first-line treatment for candidiasis with a dosing regimen equivalent to the current antifungals.

DETAILED DESCRIPTION OF THE INVENTION

The present invention relates to a pharmaceutical composition comprising i) as therapeutic active agent at least $2 \cdot 10^{10}$ CFU of lactobacilli and ii) a sulfur-containing compound as combination products for use as a first-line treatment for candidiasis and for recurrent candidiasis. The invention describes in particular vulvovaginal candidiasis and recurrent vulvovaginal candidiasis.

The term "candidiasis" refers to a fungal infection caused by yeasts of the genus *Candida*. *Candida albicans*, the most common species, is part of the usual flora of the oropharynx and of the digestive tract, and may also be present in small quantities in the normal vaginal microbiota. Vulvovaginal candidiasis is very common and may be prone to several recurrences.

By "first-line treatment of candidiasis and of recurrent candidiasis" is meant a therapeutic treatment, which is advantageously curative, having fungicidal properties for treating these candidiasis, and thus in concrete terms for destroying the pathogens at the origin of the infection. In the present case, the treatment also has fungistatic properties, characterized by inhibition of the growth of said pathogens.

According to the invention, the pathogens are members of the genus *Candida*, and preferentially of the species *Candida albicans, Candida glabrata, Candida tropicalis*, more preferentially of the species *Candida albicans*. *Candida albicans* is the most common and the best-known yeast species of the genus *Candida*. It causes fungal infections (candidiasis), for example of the gynecological mucous membranes.

Examples of candidiasis include:
Mucocutaneous candidiasis, particularly
  Oral-digestive candidiasis: oral candidiasis (thrush, glossitis, stomatitis, black hairy tongue), digestive candidiasis (esophagitis, gastroenteritis, colitis, anusitis),
  genital candidiasis: vulvitis and vulvovaginitis, balanitis and meatitis
  cutaneous candidiasis: intertrigo of the large folds (inguinal folds, intergluteal fold, sub-mammary folds and abdominal folds, armpits, diaper rash), intertrigo of the small folds (skin between the fingers)
  candidiasis of the nails: onyxis, onycholysis
Esophageal candidiasis
Systemic candidiasis The term "lactobacilli" refers to all the bacteria of the genus *Lactobacillus*, which are immobile, facultative aero-anaerobic, Gram-positive bacteria of variable shapes and sizes. Most lactobacilli convert lactose and other simple sugars into lactic acid. In the example of the treatment of VVC, lactobacilli colonize the vagina and constitute an important component of the vaginal microbiota. The present invention may thus relate to the lactobacilli constituting the vaginal microbiota, particularly *Lactobacillus casei*, and *Lactobacillus rhamnosus*.

The term "CFU" refers to the unit of measure generally recognized by the person skilled in the art for quantifying bacteria capable of establishing a colony, and means precisely "Colony Forming Unit". It is expressed in relation to the total weight of the pharmaceutical composition.

The term "pharmaceutical composition" refers to the therapeutic treatment administered to the patient. Generally, the "pharmaceutical composition" will correspond to a dose of the medicinal product. However, separate units taken at the same time, and which cumulatively would contain the products of the invention in the claimed concentrations, would not be beyond the scope of the invention. In the context of the present description, the concentrations are given for a composition corresponding to one dose, and may be adapted in other cases.

The term "combination products" means that the lactobacilli and the sulfur-containing compound, particularly thiosulfate, are formulated either in the same composition or in two separate compositions administered to the patient concomitantly, i.e., at the same time during the day.

Any interval of values indicated by the expression "between a and b" represents the range of values from more than a to less than b (i.e., the limits a and b excluded) while any interval of values indicated by the expression "from a to b" means the range of values from a to b (i.e., including the strict limits a and b).

Unless otherwise specified, all the percentages are percentages by weight.

Surprisingly, it was discovered that when these lactobacilli are used at a concentration greater than or equal to $2 \cdot 10^{10}$ CFU, in the presence of a sulfur-containing compound in a pharmaceutical composition, this composition had the capacity to inhibit quickly and specifically yeasts of the genus *Candida*. Thus, contrary to any expectation, at this concentration, the lactobacilli, potentiated by a sulfur-containing compound, can be used as a therapeutic active agent having an antifungal action. In concrete terms, it is possible to propose, instead of a chemical antifungal, the compositions according to the invention for treating candidiasis, such as vulvovaginal candidiasis and recurrent vulvovaginal candidiasis. The treatment may even consist of the lone administration of the compositions according to the invention, without administration, including prior administration, of a chemical antifungal such as fluconazole or ketoconazole. Chemical antifungals cause an imbalance of the microbiota, for example. The compositions according to the invention may thus replace the antifungals commonly administered in the treatment of these conditions. The invention thus also relates to a composition according to the invention for use as a substitute for a chemical antifungal in the treatment of candidiasis, such as vulvovaginal candidiasis and recurrent vulvovaginal candidiasis.

The composition according to the invention may be used to inhibit, in less than 24 hours and without pre-culture, pathogens of the genus *Candida*, particularly *Candida albicans* or *Candida glabrata*.

According to the invention, the therapeutic active agent having an antifungal action is a combination of lactobacilli and of a sulfur-containing compound. This combination can take the form of a single composition (simultaneous use) or of two compositions administered at the same time (combined use).

The sulfur-containing compound may be selected from an extensive list of compounds, as long as they are suitable for administration to humans or to animals.

Examples of sulfur-containing compounds include:
Sulfates, thiosulfates and polythionates (such as tetrathionates), particularly alkaline ones (sodium, potassium);
Sulfur-containing amino acids, particularly cysteine, methionine, homocysteine; oxidized derivatives thereof (for example cysteine-S-sulfonate, methionine sulfoxide); sulfur-containing amino acids linked together by a disulfide bridge (for example cystine); sulfur-containing amino acids linked via a disulfide bridge to a thiosulfate, to a sulfate, to a thiol; the derivatives of these compounds wherein the —NH— function of the amino acid is replaced by an —O— or —N(CH$_3$)— function;
Condensed amino acids (advantageously up to 5 amino acids, more advantageously up to 3 amino acids) comprising at least one sulfur-containing amino acid as defined above (for example glutathione);
Vitamins comprising sulfur in their chemical structure, such as vitamin B1 or vitamin B8;
And mixtures thereof.

When the sulfur-containing compound is thiosulfate, the composition comprises 15 to 300 mg of thiosulfate. The quantity of sulfur-containing compound other than thiosulfate will be determined by the person skilled in the art on this basis to provide an equivalent quantity of sulfur.

According to an aspect of the invention, the sulfur-containing compound is a thiosulfate, which may be selected from sodium thiosulfate or potassium thiosulfate. Preferentially, sodium thiosulfate is used. Sodium thiosulfate consists of sodium ions and thiosulfate ions.

The composition advantageously comprises 15 to 300 mg of thiosulfate, more advantageously 30 to 300 mg, still more advantageously 45 to 120 mg, still more advantageously 45 to 80 mg, and ideally 60 mg.

In an amount below 15 mg, the quantity of thiosulfate is not sufficient to potentiate the lactobacilli. In an amount above 300 mg, the thiosulfate begins to exert a deleterious inhibitory action on the endogenous or exogenous lactobacilli.

The pharmaceutical composition comprises more than $2 \cdot 10^{10}$ CFU of lactobacilli, in particular at least $3 \cdot 10^{10}$ CFU indeed at least $4 \cdot 10^{10}$ CFU of lactobacilli, advantageously at least $5 \cdot 10^{10}$ CFU of lactobacilli, more advantageously more than $1 \cdot 10^{11}$ CFU of lactobacilli. The quantity of lactobacilli advantageously varies from $2 \cdot 10^{10}$ to $1 \cdot 10^{12}$ CFU, more advantageously from $5 \cdot 10^{10}$ to $1 \cdot 10^{12}$ CFU, more advantageously from $1 \cdot 10^{11}$ to $1 \cdot 10^{12}$ CFU.

In a quantity below $2 \cdot 10^{10}$ CFU of lactobacilli, no inhibitory effect on the pathogens is observed without preliminary culture of the strain, which does not make it possible to envisage an action in treatment, in particular in first-line treatment.

In particular, for quantities of about $5 \cdot 10^{10}$ CFU of lactobacilli or more, an inhibitory effect is observed as of 24 hours. According to a particular embodiment of the invention, the pharmaceutical composition comprises $3 \cdot 10^{10}$ CFU to $7 \cdot 10^{10}$ CFU of lactobacilli, more preferentially about $5 \cdot 10^{10}$ CFU.

These quantities correspond to the general case of a composition corresponding to one dose, and may be adapted to other cases.

The composition is advantageously prepared from a lyophilizate comprising the lactobacilli and the sulfur-containing compound, advantageously thiosulfate.

In a first variant, the sulfur-containing compound, advantageously thiosulfate, is introduced during the lyophilization of the lactobacilli.

Advantageously, the composition comprises from 250 to 2500 mg of lyophilizate, more advantageously from 500 to 1500 mg of lyophilizate; the lyophilizate comprising the lactobacilli and the sulfur-containing compound, advantageously thiosulfate.

The person skilled in the art, specialist in lyophilization, will be able to adapt the quantity of the sulfur-containing compound added before lyophilization to obtain the desired quantity in the final powder obtained after lyophilization.

In a second variant, the lactobacilli are lyophilized in the absence of the sulfur-containing compound, advantageously thiosulfate, which is introduced into the pharmaceutical composition or is co-administered with the composition comprising the lactobacilli lyophilizate.

Advantageously, the pharmaceutical composition comprises
from 250 to 2500 mg of lyophilizate, more advantageously from 500 to 1500 mg of lyophilizate; the lyophilizate comprising the lactobacilli;
from 15 to 300 mg of thiosulfate, more advantageously from 30 to 300 mg, still more advantageously 45 to 120 mg, still more advantageously 45 to 80 mg, and ideally 60 mg of thiosulfate.

In a third variant, the first and second variants are combined: part of the sulfur-containing compound is introduced during lyophilization, the other part during the formulation of the pharmaceutical composition. The person skilled in the art will be able to adapt the quantities on the basis of the quantities described above in the first and second variants.

According to a preferred aspect of the invention, the lactobacilli are *Lactobacillus rhamnosus* and/or *Lactobacillus crispatus* and/or *Lactobacillus casei* and/or *Lactobacillus vaginalis*. Advantageously, the lactobacilli are *Lactobacillus rhamnosus* and/or *Lactobacillus crispatus* and/or

*Lactobacillus casei*. The preferred strain is *Lactobacillus Rhamnosus* LCR35® (*Lactobacillus rhamnosus*)(7).

Preferably, the lactobacilli are in lyophilized form. The strain may be the only lyophilized element of the composition, but preferably the strain is lyophilized in a medium comprising additional components, which will be added before or after the lyophilization step. In one variant, the sulfur-containing compound may be added before lyophilization. In another variant, the sulfur-containing compound is added after lyophilization during the preparation of the pharmaceutical composition.

According to another particular aspect of the invention, the pharmaceutical composition further comprises a preservation matrix and/or excipients well-known to the person skilled in the art, and optionally other active ingredients having a complementary action.

In particular, this composition may comprise the following active ingredients: hormones (estriol, progesterone, etc.), anti-inflammatory agents. The person skilled in the art will be able to determine which active ingredients may be advantageously coupled with the lactobacilli. This composition also comprises, according to a specific aspect of the invention, several lactobacilli strains.

These pharmaceutical compositions are advantageously formulated for vaginal, oral or topical administration, more advantageously vaginal for vulvovaginal candidiasis. In particular, the dosage form used will be capsules, tablets, creams, liquid or oily suspensions, or any other suitable medical device. Advantageously, the dosage form used will be capsules or tablets. The person skilled in the art will be able to adapt the appropriate form to the expected therapeutic effect.

The pharmaceutical composition according to the invention is advantageously an immediate-release pharmaceutical composition, particularly an immediate-release tablet or capsule or one modified according to the desired effect.

The optimal modes of administration, dosing regimens and dosage forms of the compounds and compositions according to the invention may be determined according to the criteria generally taken into account in the establishment of a pharmaceutical treatment suited to a patient, such as, for example, the patient's age or weight, the gravity of the patient's general state, the tolerance for the treatment and the side effects observed. This patient may be a human or an animal, advantageously a human.

The invention also relates to a pharmaceutical composition comprising at least $2 \cdot 10^{10}$ CFU of lactobacilli, advantageously at least about $5 \cdot 10^{10}$ CFU of lactobacilli, and a sulfur-containing compound, advantageously thiosulfate, in particular from 15 to 300 mg of thiosulfate.

The quantity of sulfur-containing compound, other than thiosulfate, will be adapted on this basis, in sulfur equivalent.

The lactobacilli and the thiosulfate, conversely the sulfur-containing compound, are advantageously as described above.

The pharmaceutical composition advantageously comprises 30 to 300 mg, more advantageously 45 to 120 mg, still more advantageously 45 to 80 mg, and ideally 60 mg of thiosulfate.

The pharmaceutical composition advantageously comprises more than $5 \cdot 10^{10}$ CFU of lactobacilli, more advantageously more than $1 \cdot 10^{11}$ CFU of lactobacilli. In the composition, the lactobacilli content advantageously varies between $2 \cdot 10^{10}$ and $1 \cdot 10^{12}$ CFU, more advantageously from $5 \cdot 10^{10}$ to $1 \cdot 10^{12}$ CFU, more advantageously from $1 \cdot 10^{11}$ to $1 \cdot 10^{12}$ CFU.

According to a particular embodiment of the invention, the composition comprises about $5 \cdot 10^{10}$ CFU of lactobacilli.

The pharmaceutical composition advantageously comprises:
- from 250 to 2500 mg of lyophilizate, more advantageously from 500 to 1500 mg of lyophilizate, the lyophilizate comprising the lactobacilli, and the composition comprises more than $2 \cdot 10^{10}$ CFU of lactobacilli, advantageously at least about $5 \cdot 10^{10}$ CFU of lactobacilli;
- from 15 to 300 mg of thiosulfate, more advantageously from 30 to 300 mg, still more advantageously 45 to 120 mg, still more advantageously 45 to 80 mg, and ideally 60 mg of thiosulfate The pharmaceutical composition is advantageously an immediate-release pharmaceutical composition, particularly an immediate-release tablet or capsule. According to another embodiment of the invention, the pharmaceutical composition is advantageously a controlled-release pharmaceutical composition, in particular a controlled-release tablet or capsule.

By "controlled-release" is meant in particular that the release of the *Lactobacillus* strain is rapid and also progressive over at least 24 hours. The terms "controlled-release" and "sustained-release" are sometimes used interchangeably.

In a particular embodiment, the immediate-release tablet according to the invention is combined with a sustained-release formulation also comprising lactobacilli according to the invention.

Thus, the invention also relates to a multilayer tablet comprising:
- at least one immediate-release layer comprising, in relation to the total weight of all the immediate-release layers, more than $2 \cdot 10^{10}$ CFU of lactobacilli, advantageously at least about $5 \cdot 10^{10}$ CFU of lactobacilli, and 15 to 300 mg of thiosulfate (or an equivalent quantity of a sulfur-containing compound);
- at least one sustained-release layer, comprising, in relation to the total weight of all the sustained-release layers, $1 \cdot 10^{5}$, preferably $1 \cdot 10^{7}$ to $1 \cdot 10^{10}$ CFU of lactobacilli.

The sustained-release layer(s) may also contain thiosulfate, advantageously in a combined quantity of 60 mg per composition.

The sustained-release layer(s) advantageously comprise a suitable excipient for conferring upon said tablet properties of mucoadhesion to the vaginal wall and of sustained release.

Examples of excipients which may be suitable are described in Advanced Drug Delivery System Reviews, 57 (2005), 1692-1712. The excipient may be selected from chitosan and derivatives thereof, pectins, polyethylene glycols, sodium alginate, polyacrylic acids, cellulose derivatives such as sodium carboxymethylcellulose, hydroxypropylmethylcellulose or microcrystalline cellulose, gums, Carbopol® polymers and combinations thereof. Preferably, the tablet according to the present invention comprises a cellulose derivative, in particular hydroxypropylmethylcellulose (HPMC).

In the context of the invention, the use of high-viscosity hydroxypropylmethylcellulose is preferred. Thus, hydroxypropylmethylcellulose having a dynamic viscosity higher than 10,000 mPa·s, advantageously between 11,000 mPa·s and 21,000 mPa·s, more advantageously of about 15,000 mPa·s, advantageously is used.

The viscosity of this well-known excipient is measured according to the European or the American standard for a 2% (w/v) aqueous solution of hydroxypropylmethylcellulose at 20° C.

The sustained-release layer generally comprises from 10 to 40% by weight in relation to the total weight of said the layer of an excipient conferring upon the tablet properties of mucoadhesion to the vaginal wall and of sustained release. Preferably, the layer comprises from 10 to 30% by weight in relation to the total weight of said layer of said excipient, more advantageously from 10 to 25% by weight, still more advantageously from 10 to 20% by weight, indeed it comprises 10% by weight of said excipient. Said excipient is advantageously HPMC.

The immediate-release layer(s) advantageously comprise(s) the compounds described above for the pharmaceutical composition, in the quantities indicated above.

The invention also relates to a method for treating candidiasis, advantageously vulvovaginal candidiasis and recurrent vulvovaginal candidiasis, comprising the administration, advantageously the first-line administration, to a patient in need thereof, of a pharmaceutical composition as described above.

The treatment of candidiasis, advantageously of vulvovaginal candidiasis and of recurrent vulvovaginal candidiasis, will be carried out preferably by administration of one dose per day. The dose may optionally be repeated, for example 2, 3, 4 or 5 days after the first dose is taken.

The treatment of candidiasis, advantageously of vulvovaginal candidiasis, and of their recurrence, may consist in:
First-line administration of the composition according to the invention, in one dose, optionally repeated, for example 2, 3, 4 or 5 days after the first dose is taken
Administration, in prevention of a recurrence, of a composition comprising lactobacilli potentiated by thiosulfate at a concentration of $10^7$ to $10^{10}$ CFU/g.

Figure 7:
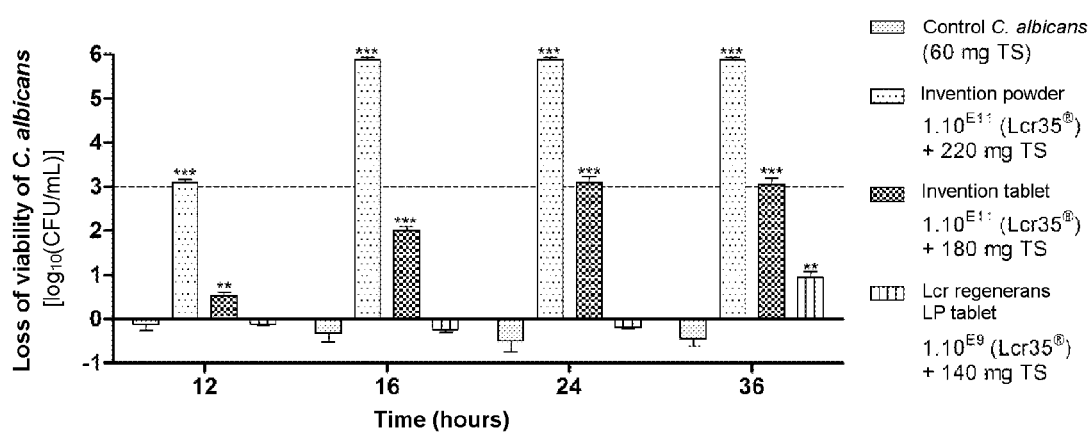

$\boxplus$ *Lactobacillus Rhamnosus* LCR35® at a concentration of $1 \cdot 10^{11}$ CFU+150 mg of glutathione FIG. 7. Activity of the invention in tablet form Loss of viability of *C. albicans* ($\log_{10}$ (CFU/mL)) as a function of co-culture time (hours) for a tablet form $\boxminus$ Control *C. albicans* (60 mg of thiosulfate);

$\boxminus$ *Lactobacillus Rhamnosus* LCR35® at a concentration of $1 \cdot 10^{11}$ CFU+220 mg of thiosulfate (invention in lyophilized powder form);

$\boxminus$ *Lactobacillus Rhamnosus* LCR35® at a concentration of $1 \cdot 10^{11}$ CFU+180 mg of thiosulfate (invention in tablet form);

$\boxminus$ *Lactobacillus Rhamnosus* LCR35® at a concentration of $10^9$ CFU+140 mg of thiosulfate as described in WO 2014/009349, formulated in tablet form.

EXAMPLES

Effect of the combination of *Lactobacillus Rhamnosus* LCR35®+ thiosulfate on pathogens of various *Candida* species Materials and Method:

After pre-culture in Sabouraud broth, the pathogen is placed with a count of about $1 \cdot 10^8$ CFU/mL in 30 mL of SVF (medium for simulating the vaginal environment pH 4.2) and put in direct contact with the lactobacilli in lyophilized form following a step of fermentation and of lyophilization+ sulfur-containing molecule (thiosulfate or cysteine) (without pre-culture so as to approach the conditions of use in vivo). The pathogen is counted on agar at $T_0$, $T_{12\,h}$, $T_{16\,h}$, $T_{20\,h}$, $T_{24\,h}$ and, in addition, at $T_{36\,h}$ for FIGS. 1, 3 and 7. The results are expressed as the logarithmic decrease between the initial count (To) and the sampling points. Antifungal activity is determined to be specific as of a decrease of 3 log. A pathogen viability control is prepared in parallel under the same conditions without the presence of compounds of the invention.

The expression "Formulation A of the invention WO2014/ 009349" refers to a formulation of the *Lactobacillus Rhamnosus* LCR35® strain as prepared by the process described in Example 4 of the application WO2014/009349, i.e., in the presence of 113 g/L of sodium thiosulfate during lyophilization. In the following examples, Formulation A comprises $1 \cdot 10^9$ CFU of *Lactobacillus Rhamnosus* LCR35® (versus $1 \cdot 10^8$ CFU for the examples of WO2014/009349).

Four concentrations of lactobacilli were tested: $2.5 \cdot 10^{19}$ CFU, $5 \cdot 10^{10}$ CFU, $7.5 \cdot 10^{19}$ CFU and $>1 \cdot 10^{11}$ CFU, or per mL: $8 \cdot 10^8$ CFU/mL, $1.6 \cdot 10^9$ CFU/mL, $2.5 \cdot 10^9$ CFU/mL and $3.3 \cdot 10^9$ CFU/mL, as well as the concentration found in Formulation A of the invention WO2014/009349 of $10^9$ CFU or $3.3 \cdot 10^7$ CFU/mL.

Various concentrations of sodium thiosulfate in the test culture medium were tested: 0, 1, 2.5, 7.5 and 10 g/L.

Several pathogens derived from clinical samples were tested: *Candida albicans, Candida glabrata, Candida tropicalis, Aspergillus fumigatus*, as well as a reference yeast, *Saccharomyces cerevisiae*.

Several lactobacilli species were tested: *L. crispatus, L. casei*.

The results are presented in FIGS. 1 to 6.

Preparation of Tablets

The tablet of the present invention is a single-layer tablet formulated to obtain a controlled release of the *Lactobacillus Rhamnosus* LCR35® strain at a concentration greater than or equal to $1 \cdot 10^{11}$ CFU/g and a quantity of thiosulfate of 180 mg. The weight of the tablet is about 950 mg.

The tablets are prepared using an industrial-size tablet press with a compression force on the order of 20 kN.

Conclusions

Figure 1:
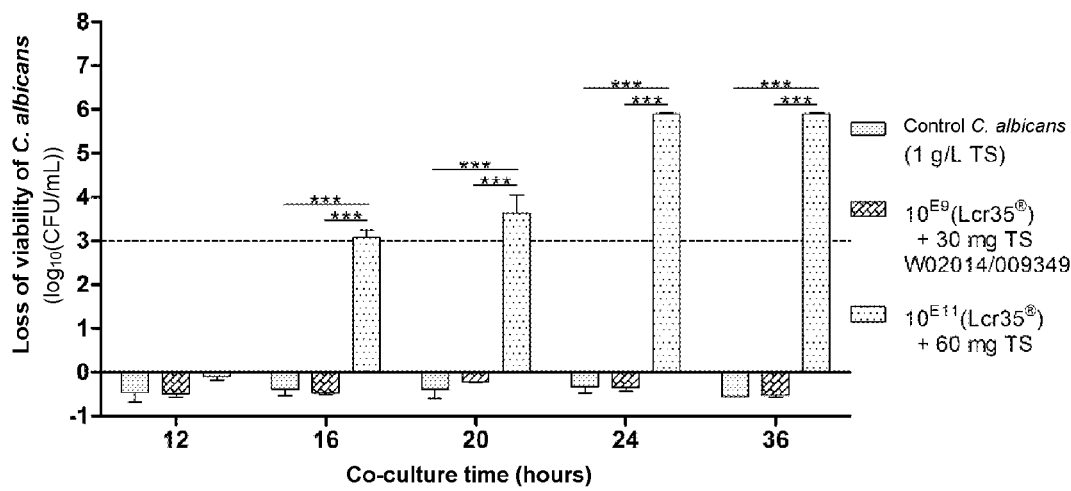
FIG. 1. Impact of a standard concentration (WO2014/009349 versus the invention)
Loss of viability of *C. albicans* ($\log_{10}$ (CFU/mL)) as a function of co-culture time (hours)
▨ *Lactobacillus Rhamnosus* LCR35® at a concentration of $10^9$ CFU+30 mg of thiosulfate as described in WO 2014/009349;
▭ *Lactobacillus Rhamnosus* LCR35® at a concentration of $10^{11}$ CFU+60 mg of thiosulfate.

FIG. 1: The invention makes it possible to have an inhibition higher than 3 log as of 20 hours of co-culture whereas the product from the prior invention (Formulation A described in WO 2014/009349) induces no antifungal effect on the pathogen *Candida albicans* ATCC10231.

Figure 2:
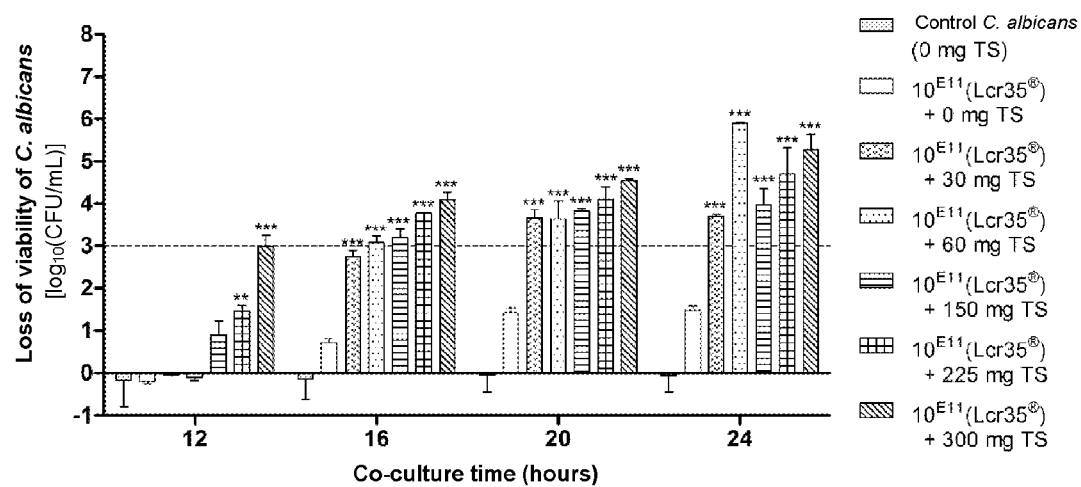
FIG. 2. Effect of the combination of *L. rhamnosus Lactobacillus Rhamnosus* LCR35® at $10^{11}$ CFU+thiosulfate at various concentrations
Loss of viability of *C. albicans* ($\log_{10}$ (CFU/mL)) as a function of co-culture time (hours)
▭ Control *C. albicans* (30 mg of thiosulfate);
▭ *Lactobacillus Rhamnosus* LCR35® at a concentration of $10^{11}$ CFU+0 mg of thiosulfate;
▭ *Lactobacillus Rhamnosus* LCR35® at a concentration of $10^{11}$ CFU+30 mg of thiosulfate;
▭ *Lactobacillus Rhamnosus* LCR35® at a concentration of $10^{11}$ CFU+60 mg of thiosulfate;
▭ *Lactobacillus Rhamnosus* LCR35® at a concentration of $10^{11}$ CFU+150 mg of thiosulfate;
▭ *Lactobacillus Rhamnosus* LCR35® at a concentration of $10^{11}$ CFU+225 mg of thiosulfate;
▭ *Lactobacillus Rhamnosus* LCR35® at a concentration of $10^{11}$ CFU+300 mg of thiosulfate FIG. 3. Effect of the combination of *Lactobacillus Rhamnosus* LCR35® at various concentrations+60 mg of thiosulfate
Loss of viability of *C. albicans* ($\log_{10}$ (CFU/mL)) as a function of co-culture time (hours)
▭ Control *C. albicans* (60 mg of thiosulfate);
▨ *Lactobacillus Rhamnosus* LCR35® at a concentration of $2.5 \cdot 10^{19}$ CFU+60 mg of thiosulfate
▭ *Lactobacillus Rhamnosus* LCR35® at a concentration of $5 \cdot 10^{10}$ CFU+60 mg of thiosulfate;
▭ *Lactobacillus Rhamnosus* LCR35® at a concentration of $7.5 \cdot 10^{10}$ CFU+60 mg of thiosulfate;
▭ *Lactobacillus Rhamnosus* LCR35® at a concentration of $1 \cdot 10^{11}$ CFU+60 mg of thiosulfate.

FIG. 2. As of 1 g/L of thiosulfate (range tested from 1 to 10 g/L), the invention makes it possible to have an inhibition higher than 3 log as of 20 hours of co-culture. At the optimal concentration of 2 g/L, this level of antifungal effect is reached as of 16 hours of co-culture between the invention and the pathogen *Candida albicans* ATCC10231.

Figure 3:
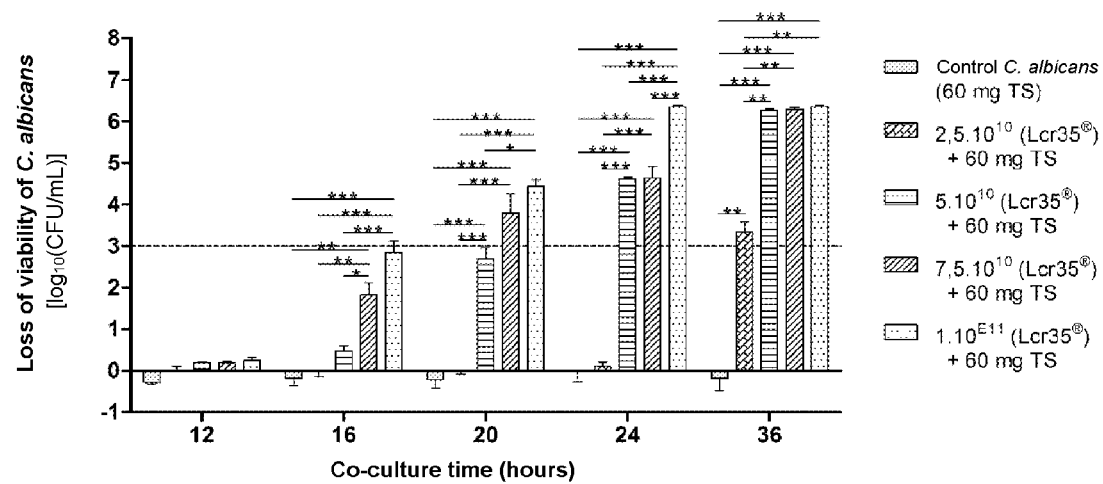

FIG. 3: An antifungal activity of 3 log is obtained in 24 hours starting with an *Lactobacillus Rhamnosus* LCR35® concentration of $5 \cdot 10^{10}$ CFU (or $1.6 \cdot 10^9$ CFU/mL). For a concentration of $2.5 \cdot 10^{10}$ CFU (or $8 \cdot 10^8$ CFU/mL), this antifungal activity is obtained after 36 hours of co-culture between the invention and the pathogen *Candida albicans* ATCC10231.

Figure 4:
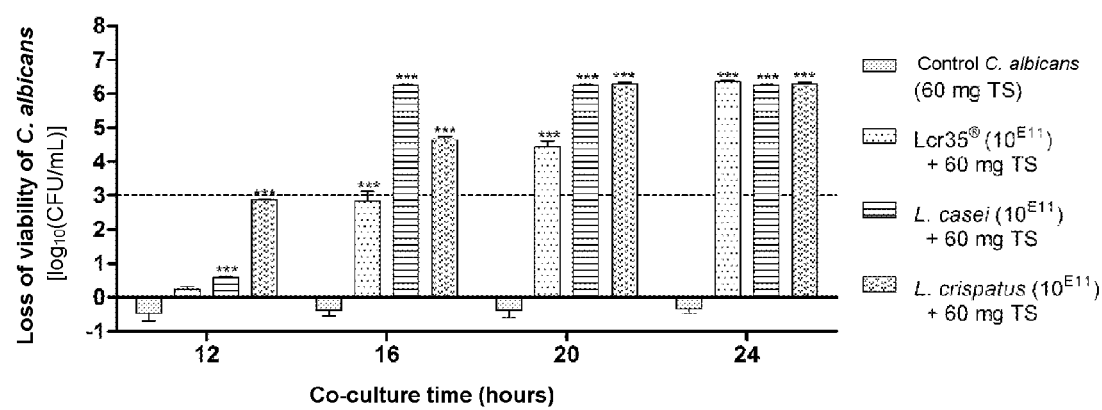
FIG. 4. Effect of the combination of *Lactobacillus* spp. at $10^{11}$ CFU+60 mg of thiosulfate on *Candida albicans*.
Loss of viability of *C. albicans* ($\log_{10}$ (CFU/mL)) as a function of co-culture time (hours)
▭ Control *C. albicans* (60 mg of thiosulfate);
▭ *Lactobacillus Rhamnosus* LCR35® at a concentration of $1 \cdot 10^{11}$ CFU+60 mg of thiosulfate;
▭ *L. casei* at a concentration of $1 \cdot 10^{11}$ CFU+60 mg of thiosulfate;
▭ *L. crispatus* at a concentration of $1 \cdot 10^{11}$ CFU+60 mg of thiosulfate FIG. 5. Effect of the combination of *Lactobacillus Rhamnosus* LCR35® at $10^{11}$ CFU+60 mg of thiosulfate on *Candida* spp.
5A: Loss of viability of clinical *Candida albicans* ($\log_{10}$ (CFU/mL)) as a function of co-culture time (hours)
▭ Control clinical *C. albicans* (60 mg of thiosulfate);
▭ *Lactobacillus Rhamnosus* LCR35® at a concentration of $1 \cdot 10^{11}$ CFU+60 mg of thiosulfate
5B: Loss of viability of clinical *Candida glabrata* ($\log_{10}$ (CFU/mL)) as a function of co-culture time (hours)
▭ Control clinical *C. glabrata* (60 mg of thiosulfate);
▨ *Lactobacillus Rhamnosus* LCR35® at a concentration of $1 \cdot 10^{11}$ CFU+60 mg of thiosulfate
5C: Loss of viability of *Aspergillus fumigatus* ($\log_{10}$ (CFU/mL)) as a function of co-culture time (hours)
▭ Control *A. fumigatus* (60 mg of thiosulfate);
▭ *Lactobacillus Rhamnosus* LCR35® at a concentration of $1 \cdot 10^{11}$ CFU+60 mg of thiosulfate
5D: Loss of viability of *Saccharomyces cerevisiae* ($\log_{10}$ (CFU/mL)) as a function of co-culture time (hours)
▭ Control *S. cerevisiae* (60 mg of thiosulfate);
▭ *Lactobacillus Rhamnosus* LCR35® at a concentration of $1 \cdot 10^{11}$ CFU+60 mg of thiosulfate FIG. 6. Effect of the combination of *Lactobacillus Rhamnosus* LCR35® at $10^{11}$ CFU+sulfur-containing molecules on *Candida albicans*.
Loss of viability of *C. albicans* ($\log_{10}$ (CFU/mL)) as a function of co-culture time (hours)
6A: Effect of the combination of *Lactobacillus Rhamnosus* LCR35® at $10^{11}$ CFU+60 mg of thiosulfate
▭ Control *C. albicans* (60 mg of thiosulfate);
▭ *Lactobacillus Rhamnosus* LCR35® at a concentration of $1 \cdot 10^{11}$ CFU+60 mg of thiosulfate
6B: Effect of the combination of *Lactobacillus Rhamnosus* LCR35® at $10^{11}$ CFU+60 mg of cysteine
▭ Control *C. albicans* (60 mg of cysteine);
▭ *Lactobacillus Rhamnosus* LCR35® at a concentration of $1 \cdot 10^{11}$ CFU+60 mg of cysteine
6C: Effect of the combination of *Lactobacillus Rhamnosus* LCR35® at $10^{11}$ CFU+150 mg of glutathione
▭ Control *C. albicans* (60 mg of glutathione)
Figure 5A:
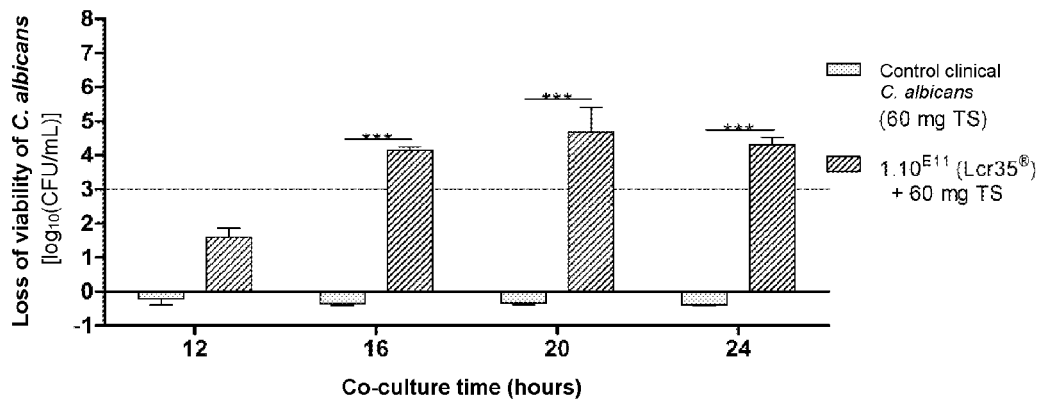
Figure 5B:
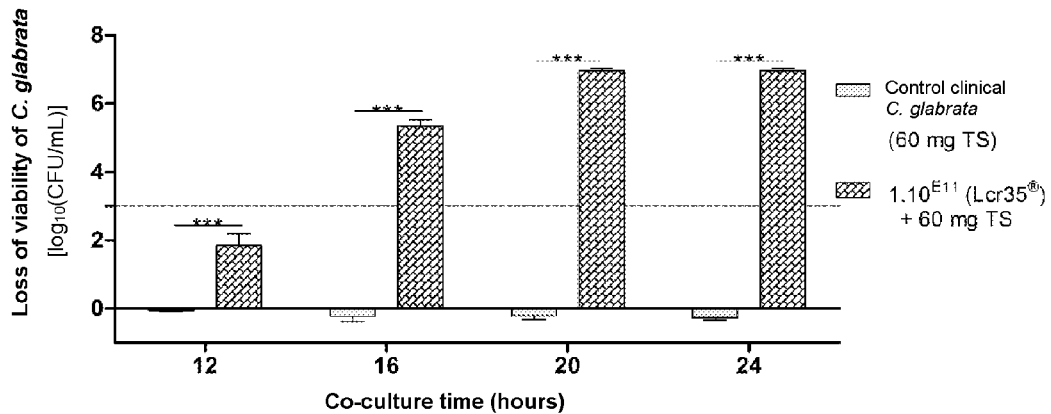
Figure 5C:
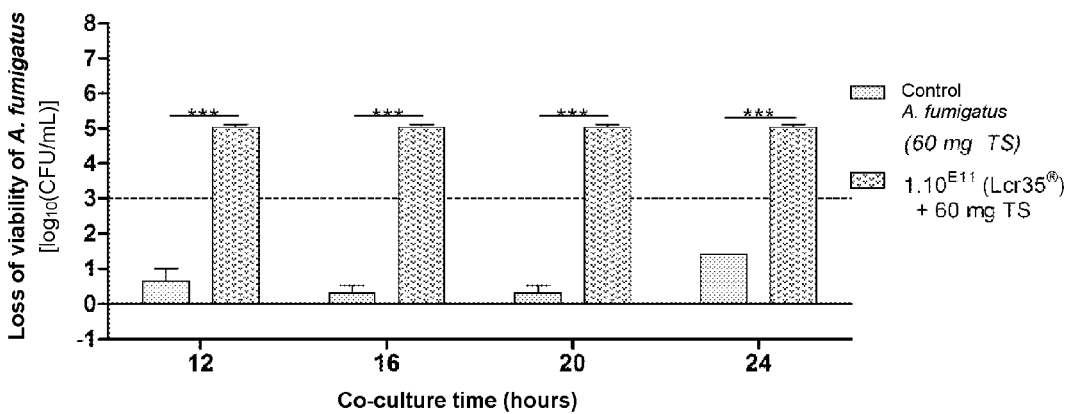
Figure 5D:
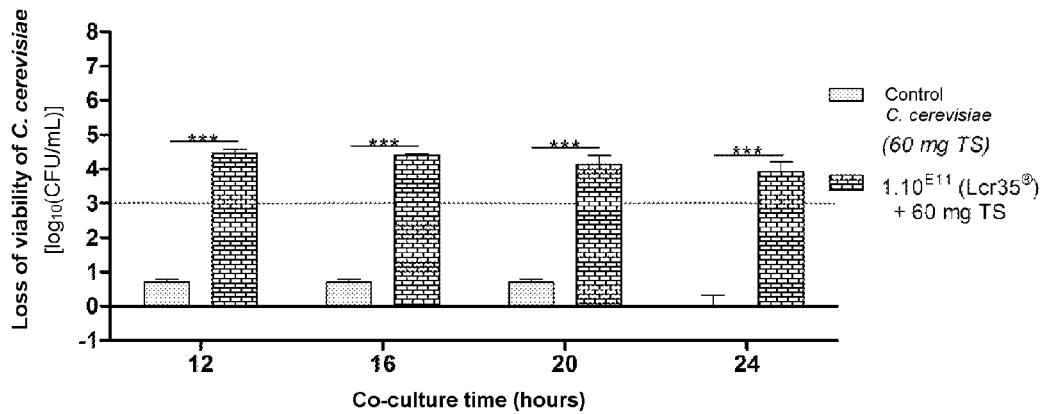

FIG. 4: The antifungal activity of the invention is demonstrated as of 20 hours for various lactobacilli species for the pathogen *Candida albicans* ATCC10231 in co-culture.

FIG. 5: The antifungal activity of the invention is demonstrated as of 16 hours for various species: two pathogenic clinical strains: *Candida albicans* and *Candida glabrata*; one pathogenic strain: *Aspergillus fumigatus*; and one yeast strain: *Saccharomyces cerevisiae*.

Figure 6A:
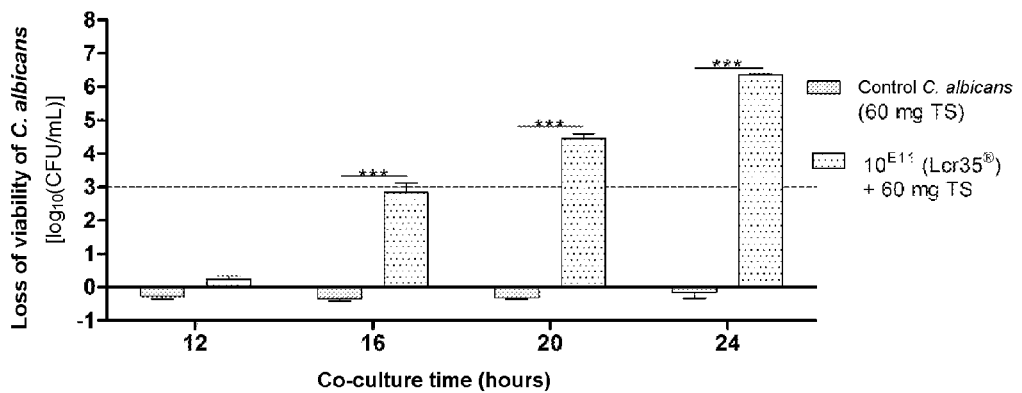
Figure 6B:
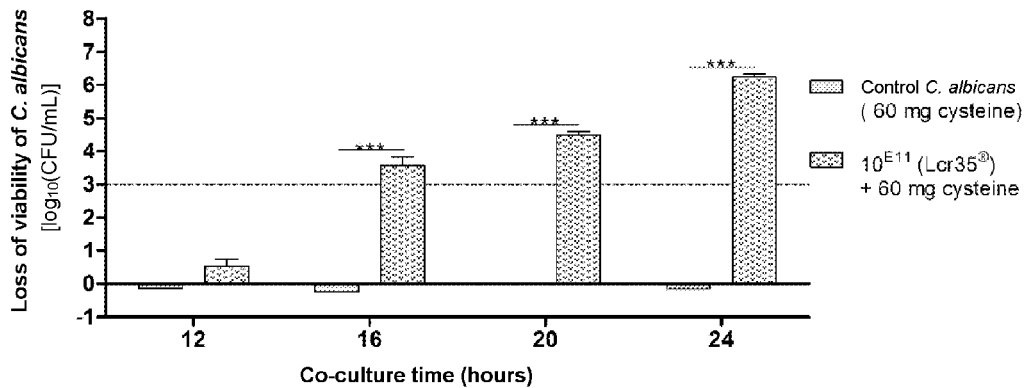
Figure 6C:
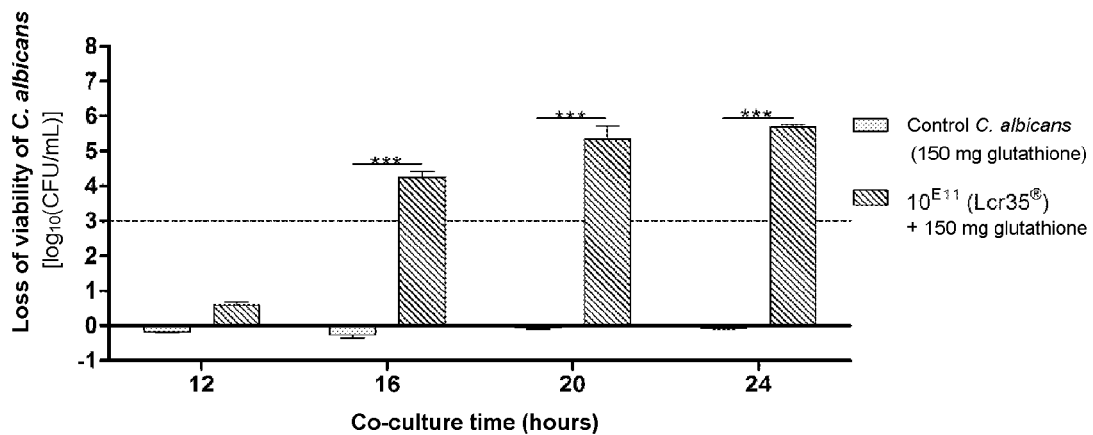

FIG. 6: The antifungal activity of the invention is demonstrated as of 16 hours for various sources of sulfur-containing molecules (thiosulfate, cysteine, glutathione) compared with the pathogen *Candida albicans* ATCC10231 in co-culture.

FIG. 7: The antifungal activity is retained after formulation as controlled-release tablets.

BIBLIOGRAPHICAL REFERENCES

Publications

1. Sobel J D. Recurrent vulvovaginal candidiasis. A prospective study of the efficacy of maintenance ketoconazole therapy. N Engl J Med 1986; 315: 1455-58.
2. Fischer G. Chronic vulvovaginal candidiasis: what we know and what we have yet to learn. Australas J Dermatol, 2012 November; 53(4):247-54. doi: 10.1111/j.1440-0960.2011.00860.x. Epub 2012 Sep. 24
3. Petrova et al. *Lactobacillus* species as biomarkers and agents that can promote various aspects of vaginal health. Frontiers in Physiology. 2015.
4. Kern et al. Preventive treatment of vulvovaginal candidosis with vaginal probiotic (Gynophilus®-Lcr Regenerans®) results of the observational study candiflore. La letter du Gynecologue no. 370—March 2012
5. Yue et al. The dynamic changes of vaginal microecosystem in patients with recurrent vulvovaginal candidiasis; a retrospective study of 800 patients. Arch Gynecol Obstet DOI 10.1007/s00404-015-3774-2
6. Murina et al. Can *Lactobacillus fermentum* LF10 and *Lactobacillus acidophilus* LA02 in a slow-release vaginal product be useful for prevention of recurrent vulvovaginal candidiasis? A clinical study. J Clin Gastroenterol. Volume 48, sup. 1; November/December 2014

7. Sophie Coudeyras et al. Taxonomic and strain-specific identification of the probiotic strain *Lactobacillus rhamnosus* 35 within the *Lactobacillus casei* group, Appl. Environ. Microbiol. doi:10.1128/AEM.02286-07, 2008.

PATENTS AND PATENT APPLICATIONS

U.S. Pat. No. 6,093,394
U.S. Pat. No. 6,468,526
U.S. Pat. No. 7,807,440
US 2010/0151026
WO 84/04675
WO 2000/035465
US 2002/0044926
WO 2006/045475
WO2014/009349
WO 2014/009330

The invention claimed is:

1. A method for first-line treatment of candidiasis in a patient in need thereof, the method comprising vaginally administering to said patient a pharmaceutical composition comprising: i) as therapeutic active agent at least $5 \times 10^{10}$ CFU of *Lactobacillus rhamnosus* 35 (Lcr35); and ii) at least 60 mg of thiosulfate, wherein the pharmaceutical composition is used as a substitute for a chemical antifungal.

2. The method of claim 1, wherein candidiasis is recurrent candidiasis.

3. The method of claim 1, wherein pathogen is selected from the group consisting of: *Candida albicans, Candida glabrata* and *Candida tropicalis*.

4. The method of claim 1, wherein the pharmaceutical composition comprises from 60 mg to 300 mg of thiosulfate.

5. The method of claim 1, wherein the pharmaceutical composition comprises from 60 to 120 mg of thiosulfate.

6. The method of claim 1, wherein the pharmaceutical composition comprises from 60 to 80 mg of thiosulfate.

7. The method of claim 1, wherein the pharmaceutical composition comprises at least $1 \times 10^{11}$ CFU of *Lactobacillus rhamnosus* 35 (Lcr35).

8. The method of claim 1, wherein the pharmaceutical composition comprises from $1 \times 10^{11}$ to $1 \times 10^{12}$ CFU of *Lactobacillus rhamnosus* 35 (Lcr35).

9. The method of claim 1, wherein the candidiasis is vulvovaginal candidiasis.

10. The method of claim 1, wherein the pharmaceutical composition is formulated to be administered in one dose, once per day.

11. The method of claim 1, wherein the pharmaceutical composition is in the form of an immediate-release tablet or capsule.

12. The method of claim 1, wherein the pharmaceutical composition is in the form of a multilayer tablet comprising:
at least one immediate-release layer comprising, in relation to the total weight of all the immediate-release layers, at least $5 \times 10^{10}$ CFU of *Lactobacillus rhamnosus* 35 (Lcr35) and 60 to 300 mg of thiosulfate; and
at least one sustained-release layer, comprising, in relation to the total weight of all the sustained-release layers, from $1 \times 10^{7}$ to $1 \times 10^{10}$ CFU of *Lactobacillus rhamnosus* 35 (Lcr35).

13. The method of claim 12, wherein in the multilayer tablet the sustained-release layer comprises from 10 to 40% by weight of hydroxypropylmethylcellulose (HPMC) in relation to the total weight of said layer.

14. A method for first-line treatment of vulvovaginal candidiasis and its recurrence in a patient in need thereof comprising vaginally administering a pharmaceutical composition comprising:
i) as therapeutic active agent at least $5 \times 10^{10}$ CFU of *Lactobacillus rhamnosus* 35 (Lcr35); and
ii) at least 60 mg of thiosulfate, optionally repeating the administration of the same pharmaceutical composition 2, 3, 4 or 5 days after the first dose is taken and administering a composition comprising *Lactobacillus rhamnosus* Lcr35 at a concentration of $10^{7}$ to $10^{10}$ CFU/g and thiosulfate to promote the prevention of recurrence of vulvovaginal candidiasis, wherein the pharmaceutical composition is used as a substitute for a chemical antifungal.

* * * * *